United States Patent
DeCesare et al.

(10) Patent No.: US 7,150,746 B2
(45) Date of Patent: Dec. 19, 2006

(54) ELECTROSURGICAL ABLATOR WITH INTEGRATED ASPIRATOR LUMEN AND METHOD OF MAKING SAME

(75) Inventors: Michael DeCesare, New Port Richey, FL (US); Hugh S. West, Jr., Sandy, UT (US)

(73) Assignee: Linvatec Corporation, Largo, FL (US)

( * ) Notice: Subject to any disclaimer, the term of this patent is extended or adjusted under 35 U.S.C. 154(b) by 301 days.

(21) Appl. No.: 10/866,014

(22) Filed: Jun. 10, 2004

(65) Prior Publication Data
US 2005/0277915 A1   Dec. 15, 2005

(51) Int. Cl.
*A61B 18/14* (2006.01)
(52) U.S. Cl. ....................................... 606/41
(58) Field of Classification Search ................... 606/41
See application file for complete search history.

(56) References Cited

U.S. PATENT DOCUMENTS

| | | |
|---|---|---|
| 3,828,780 A | 8/1974 | Morrison, Jr. |
| 4,998,933 A | 3/1991 | Eggers et al. |
| 5,178,620 A | 1/1993 | Eggers et al. |
| 5,364,395 A | 11/1994 | West, Jr. |
| 5,366,443 A | 11/1994 | Eggers et al. |
| 5,419,767 A | 5/1995 | Eggers et al. |
| 5,472,441 A | 12/1995 | Edwards et al. |
| 5,697,909 A | 12/1997 | Eggers et al. |
| 5,904,681 A | 5/1999 | West, Jr. |
| 6,190,381 B1 | 2/2001 | Olsen et al. |
| 6,238,391 B1 * | 5/2001 | Olsen et al. ................... 606/41 |
| 6,254,600 B1 * | 7/2001 | Willink et al. ................ 606/41 |
| 6,296,638 B1 | 10/2001 | Davison et al. |
| 6,379,350 B1 * | 4/2002 | Sharkey et al. ............... 606/41 |
| 6,482,201 B1 | 11/2002 | Olsen et al. |
| 6,565,561 B1 * | 5/2003 | Goble et al. .................. 606/41 |
| 6,589,237 B1 | 7/2003 | Woloszko et al. |
| 6,618,626 B1 | 9/2003 | West, Jr. et al. |

OTHER PUBLICATIONS

Arthrocare: Multi-Electrode Technology (published on or before May 2004).

* cited by examiner

Primary Examiner—Michael Peffley
Assistant Examiner—Alex Toy
(74) Attorney, Agent, or Firm—Workman Nydegger

(57) ABSTRACT

Electrosurgical devices for ablating tissue and methods of making the same are disclosed. The electrosurgical devices include an electrode with a lumen for aspirating gasses and debris produced during surgery. The electrode also includes a plurality of upper active edges for ablating tissue in an electrosurgical procedure. The upper active electrodes are spaced apart to form a filter that filters out large tissue particles from being aspirated into the lumen. The upper active edges ablate the large particles to form particles that can pass into the lumen. A lower active edge is formed at the terminal end of the lumen for ablating tissue being aspirated into the lumen. The lower active edge prevent tissue particles from occluding the opening to the lumen.

22 Claims, 4 Drawing Sheets

US 7,150,746 B2

ELECTROSURGICAL ABLATOR WITH INTEGRATED ASPIRATOR LUMEN AND METHOD OF MAKING SAME

BACKGROUND OF THE INVENTION

1. The Field of the Invention

The present invention relates to electrosurgical devices for ablating tissue in an arthroscopic procedure. More specifically, the present invention relates to electrosurgical devices with an electrode that defines a lumen for aspirating gasses and debris.

2. The Relevant Technology

An arthroscope is an instrument used to look directly into a surgical site. Typically, the arthroscope utilizes a magnifying lens and coated glass fibers that beam an intense, cool light into the surgical site. A camera attached to the arthroscope allows the surgeon to view the surgical site on a monitor in the operating room. With the arthroscope, the surgeon can look directly into a surgical site, such as a knee or shoulder, to diagnose injury and decide on the best treatment. While viewing the surgical site with the arthroscope, the surgeon can repair an injury using a separate surgical instrument.

The ability to view the surgical site in this manner allows for a minimally invasive procedure. In recent years, arthroscopic surgeries have been developed for surgical procedures that traditionally were once very complicated and time consuming. Many of these surgeries are now performed as outpatient procedures using arthroscopic techniques.

At the beginning of the arthroscopic procedure, the patient receives an anesthetic. After the patient has been sufficiently anesthetized, the surgeon makes a plurality of incisions, known as portals. The portals extend from the exterior of the body of the patient to the surgical site. Three portals are usually made: a first for the arthroscope, a second for the surgical instrument, and a third to permit fluids to escape from the surgical site.

Sterile fluid is generally introduced by way of the arthroscope through the first portal. The sterile fluid serves among other purposes to expand the area of the surgical site. The insertion of sterile fluid makes it easier to see and work inside the body of the patient at the surgical site.

Electrosurgical instruments are a common device used in arthroscopy to ablate and/or coagulate tissue. In electrosurgery, an electrode is used to direct a high frequency current near or through body tissue. The high frequency current generates enough heat to ablate tissue. In monopolar electrosurgery the return electrode is a patch placed on the person. Energy that dissipates into the tissue connects the circuit by passing through the patch.

In a bipolar electrosurgical device, the return electrode is placed in a separate location on the electrosurgical device. Energy leaving the ablator electrode passes through fluids and/or tissue and returns to the electrode on the electrosurgical device.

In both monopolar and bipolar electrosurgery, an electrode transfers energy to the surrounding fluid. The energy can be controlled to simply warm the adjacent tissue or it can be used to cut or ablate tissue. Warming tissue is often done to facilitate coagulation. The heating event causes coagulation and thus can be used to stop bleeding in an arthroscopic procedure.

To ablate tissue, larger amounts of energy are applied to the electrode. The electrode generates enough heat to create gas bubbles around the electrode. The gas bubbles have a much higher resistance than tissue or saline, which causes the voltage across the electrode to increase. Given sufficient power the electrode discharges (i.e. arcs). The high voltage current travels through the gas bubbles and creates a plasma discharge. Moving the electrode close to tissue causes the plasma layer to come within a distance sufficiently close to vaporize and ablate the tissue.

The contours and surface area of an electrode are important for controlling where arcing occurs on the electrode and how much power is required to cause a discharge. Current density is greatest at sharp edges. Arcing, and thus ablating, can be controlled by forming electrodes or electrode edges with small surface areas.

Even though gas bubbles can be a necessary or unavoidable consequence of electrosurgery, gas bubbles can pose a problem for the practitioner using arthroscopy. Bubbles formed by an electrosurgical device can block the physician's view in the arthroscopic camera. Thus, bubbles collecting in the surgical site can significantly slow down the surgical procedure or increase the risk that a physician will make an undesirable cut.

To overcome the disadvantages created by bubbles formed in the surgical area, recent electrosurgical devices have been created that have lumens for aspirating gasses and tissue debris. One problem with these electrosurgical devices, however, is that they can become plugged. In operation, an electrosurgical device creates tissue fragments. These tissue fragments are drawn to the opening of the aspirating lumen and can block the passage of gasses. Some recent electrosurgical devices place electrodes above the opening of the lumen to ablate tissue blocking the opening. However, even with these electrodes, there is a period of time when the electrode is breaking down the fragment that gasses cannot pass through. When this event occurs, a surgeon has to wait for the fragment to degrade and pass before the surgeon can continue with the surgical procedure.

Therefore, what is needed is an improved electrosurgical device that can aspirate tissue fragments without disrupting the aspiration of gasses, such that a surgeon's field of vision remains clear.

BRIEF SUMMARY OF THE INVENTION

The present invention overcomes the disadvantages of the electrosurgical devices in the prior art by providing an electrode that reduces plugging. In an exemplary embodiment, the electrosurgical instrument includes a handle with a probe extending from the handle. The probe can be inserted into a patient during an arthroscopic procedure to ablate tissue.

The electrosurgical probe has an electrode on its distal end. The electrode includes an active surface for generating arcing that can be used to ablate tissue. The electrode also defines a lumen where gasses and debris can be aspirated. The lumen terminates prior to the distal end and opens into one or more openings.

The active surface of the electrode includes upper active edges and lower active edges. The upper active edges form a first layer for ablating tissue. The upper active edges are distal to the lumen and spaced apart to form a filter for filtering tissue being aspirated into the lumen. The lower active edge or edges are positioned at the terminus of the lumen and ablate tissue that passes into the lumen.

Because the upper active edges are distal to the lumen and spaced apart to form a filter, the upper active edges trap large fragments of tissue before they reach the lumen. Furthermore, tissue stuck on the upper active edges typically does not prevent gas bubbles from passing into the lumen because of the many alternative paths to the lumen through the upper edges.

Once these tissue fragments have been broken into smaller pieces, the force of the aspirator will draw the smaller fragments into the lumen. The lower active edge is formed at the distal end of the lumen to prevent the smaller fragments from collecting and forming a plug in the lumen.

The present invention advantageously prevents tissue fragments from plugging the aspirating lumen of the electrosurgical device. The continuous flow of fluids and gasses through the aspirating lumen greatly increases the ability of the physician to complete a procedure without interruption. The surgeon's clear field of vision provided by using the electrosurgical device of the present invention helps prevent errors, increases the speed with which the surgeon can complete the procedure and thus reduces the overall expense of the surgical procedure.

The method of manufacturing the electrosurgical device of the present invention provides significant advantages over the prior art. In one embodiment of the present invention, the electrode is made from a single piece of electrically conductive material. The lumen is made by back drilling a bore into the piece of material. The bore terminates proximal to the distal end. A series of grooves are then cut into the distal end. The grooves are cut deep enough to reach the lumen, thereby creating openings into the lumen. The grooves also create ribs of material. The upper edges of the ribs form active edges where the electrode arcs, thereby generating the cutting potential of the electrode.

Creating an electrode in this manner can significantly reduce the cost of manufacturing. Back drilling the bore and cutting the grooves are relatively simple and economical manufacturing procedures, yet they can produce an electrode with extensive amounts of active edges for ablating tissue.

The probe of an electrosurgical device must be very small for it to be inserted into a patient through the portals, as discussed above. Therefore, creating electrodes with a large active surface area can be particularly challenging. The problems accompanying size restriction are further compounded by adding a sizable lumen to the probe for aspirating gasses and debris. The manufacturing techniques of the present invention optimize lumen size and ablation potential.

The active area of the electrode is maximized by placing the lumen blow the active area. The placement of the lumen allows for a greater ablation surface, yet the configuration of the ablation surfaces helps prevent clogging of the lumen as compared with prior art devices.

These and other features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF EXEMPLARY EMBODIMENTS

Figure 1:
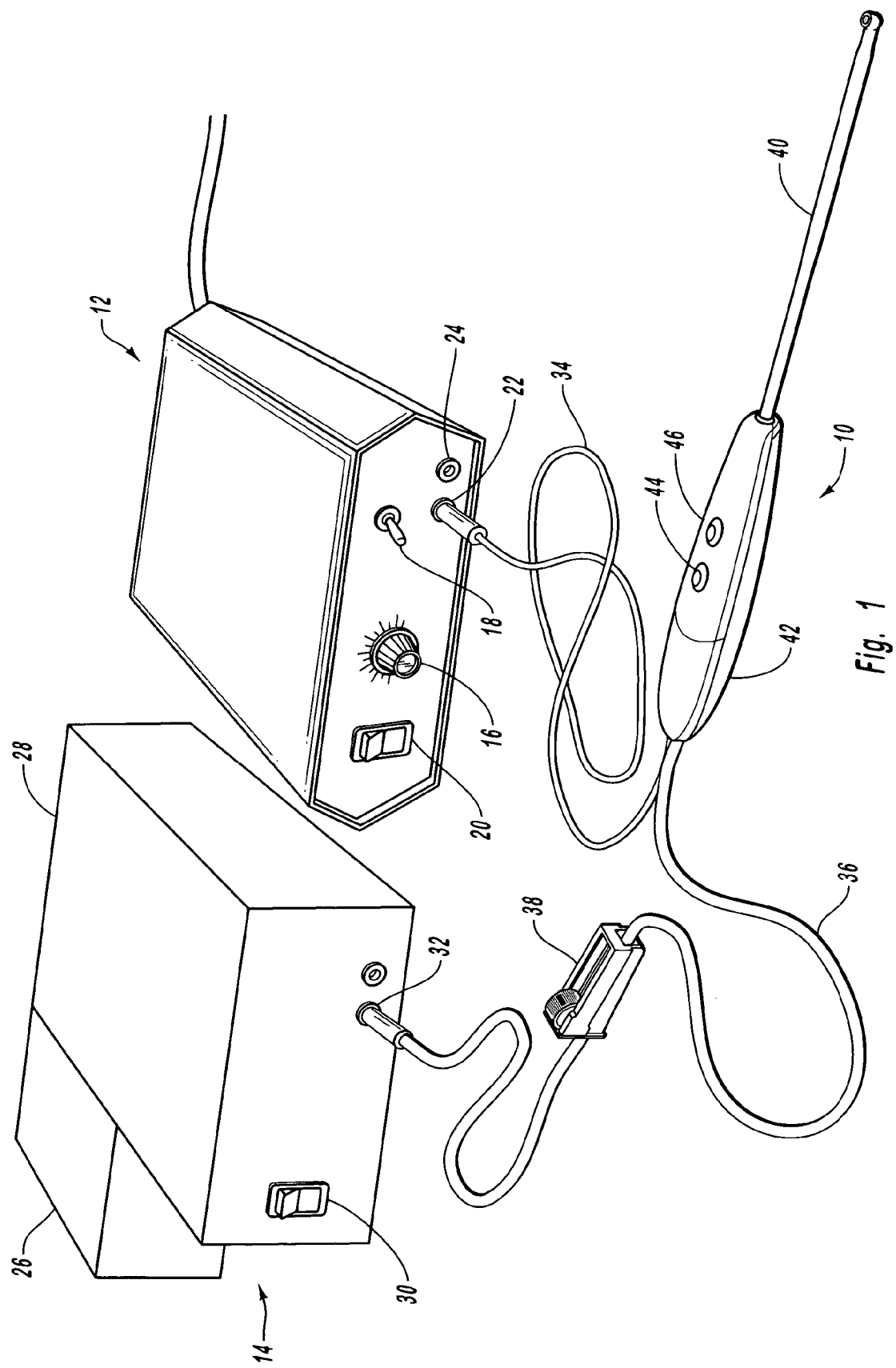
FIG. 1 is a perspective view of an electrosurgical system including a radio frequency generator, an aspirator, and an electrosurgical instrument according to an exemplary embodiment of the present invention.

Embodiments of the present invention relate to electrosurgical systems for ablating tissue in an electrosurgical procedure. FIG. 1 shows an exemplary electrosurgical system which includes an electrosurgical instrument 10 connected to an electrosurgical generator 12 and an aspirator 14.

In an exemplary embodiment, electrosurgical generator 12 is configured to generate radio frequency ("RF") wave forms for a monopolar instrument such as electrosurgical instrument 10. Generator 12 can generate energy useful for ablating tissue and/or coagulating tissue. In one embodiment, generator 12 includes standard components, such as dial 16 for controlling the frequency and/or amplitude of the RF energy, a switch 18 for changing the type of waveform generated, a switch 20 for turning the generator on and off, and an electrical port 22 for connecting the electrosurgical instrument 10. Generator 12 also includes port 24 for connecting an electrical ground. It will be appreciated that generator 12 can be designed for use with bipolar electrosurgical instruments instead of, or in addition to, monopolar devices.

Aspirator 14 includes a pump 26, a reservoir 28, an on/off switch 30, and an aspirator port 32. Pump 26 provides negative pressure for aspirating fluids, gasses, and debris through electrosurgical device 10. Aspirated fluids and debris can be temporarily stored in reservoir 28. In another embodiment, electrosurgical device 10 is connected to wall suction. When using wall suction, canisters or other reservoirs are placed in the suction line to collect aspirated tissue and fluids. Those skilled in the art will recognize that many different configurations of generator 12 and aspirator 14 can be used in the present invention.

Electrosurgical instrument 10 includes power cord 34 for electrically connecting instrument 10 to generator 12 through electrical port 22. Extension tubing 36 provides a fluid connection between instrument 10 and aspirator 14. A flow control device 38 allows a practitioner to vary the rate of aspiration through instrument 10.

A probe 40 is connected to a handle 42. Probe 40 can be used for ablating tissue in a patient. Buttons 44 and 46 on handle 42 can be used to switch the mode of operation of probe 40 between an ablation mode and a coagulation mode.

Figure 2:
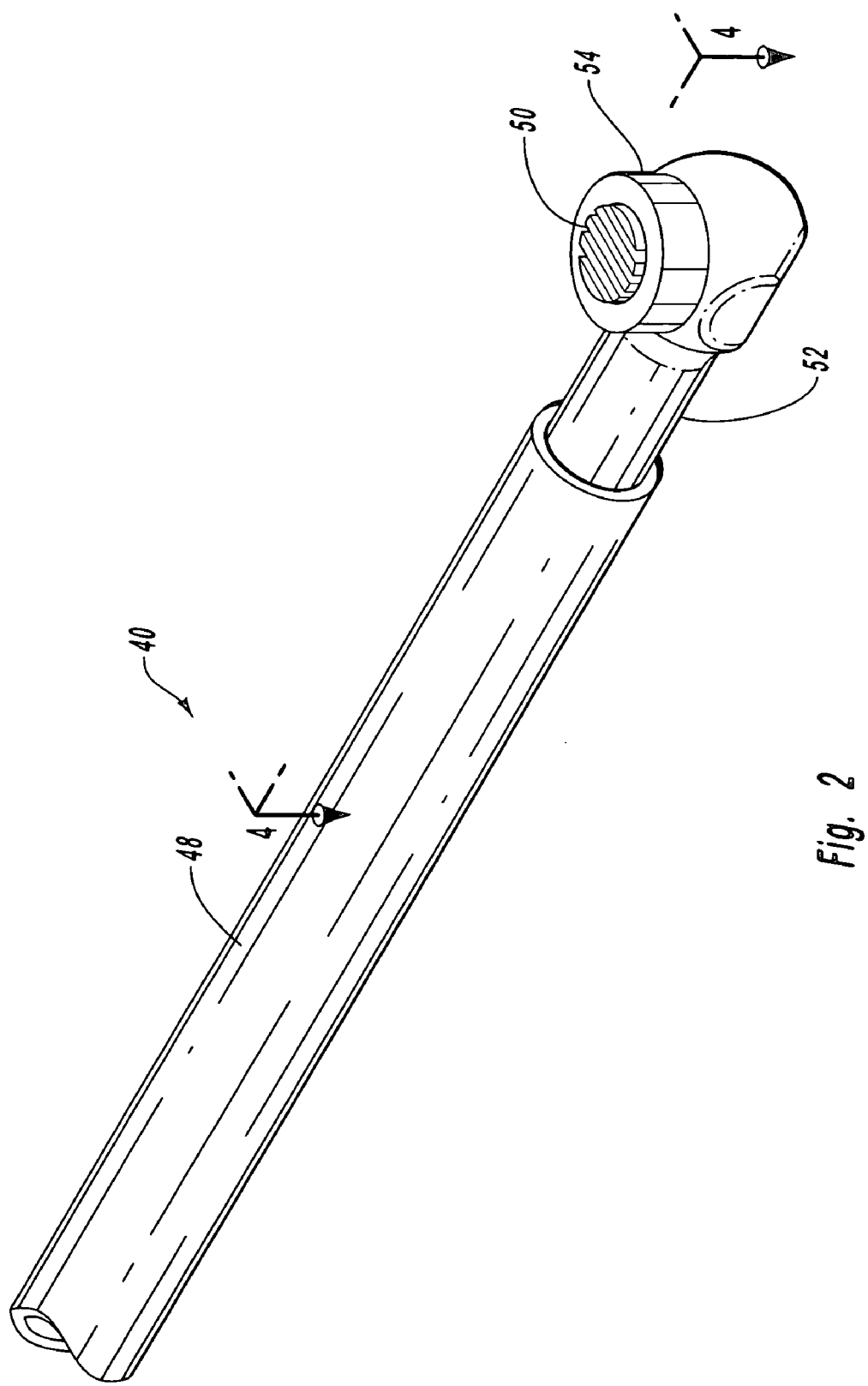
FIG. 2 is a perspective view of the probe of the electrosurgical instrument of FIG. 1.
Figure 3:
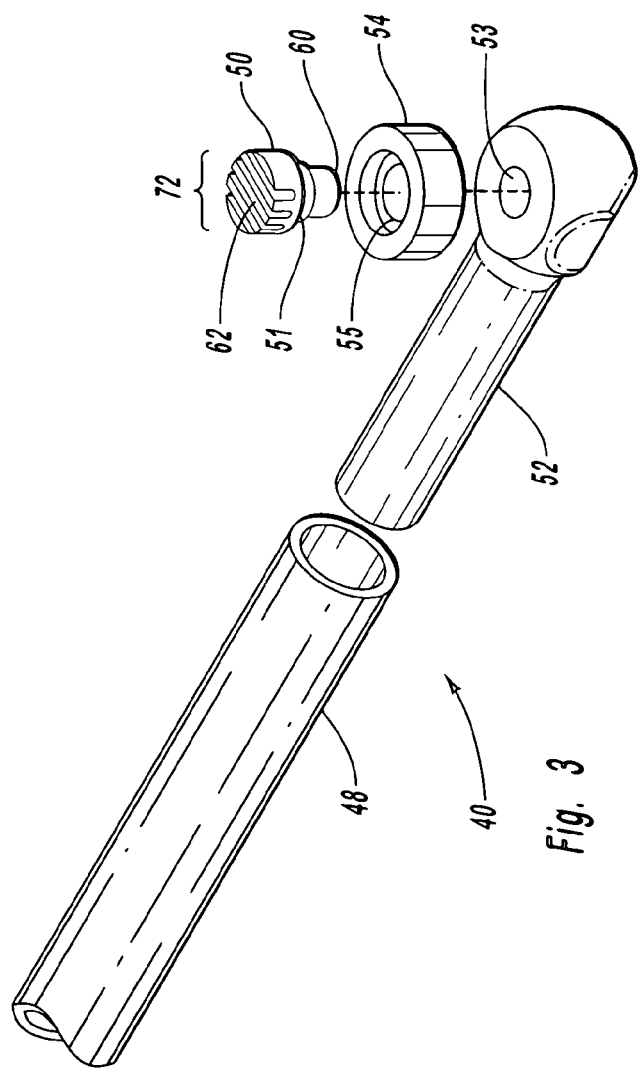
FIG. 3 is an exploded view of the probe of the electrosurgical instrument of FIG. 1.

FIGS. 2 and 3 illustrates probe 40 of the present invention with the insulating layer 56 removed (See FIG. 4) to show various underlying aspects of the invention. As shown in the exemplary embodiment of FIG. 2, probe 40 includes tubing 48, an electrode 50, an electrode seat 52, and an insulating piece 54.

Electrode 50, shown in FIG. 3, has a distal end 60 and a proximal end 62. As discussed more fully below, active surface 72 is formed on distal end 62. Active surface 72 is configured to arc when high powered RF energy is supplied to it. Arcing on active surface 72 gives electrode 50 the ability to ablate tissue.

Electrode 50 can also be used to coagulate tissue. Coagulation can be performed by reducing the power supplied to the active surface 72 to a level below that needed to cause the active surface 72 to arc. Current that flows through electrode 50 without arcing creates heat, but in lesser amounts. The lesser energy dissipates into the surrounding tissue and facilitates coagulation. Buttons 44 and 46 (See FIG. 1) allow a surgeon to select the power level to operate in a coagulation mode or an ablation mode.

In an exemplary embodiment, insulating piece 54 comprises an annular ring configured to encircle at least a portion of electrode 50. Insulating piece 54 is typically a heat resistant and electrically nonconductive material such as a ceramic. Insulating piece 54 is configured to seat against electrode 50 to prevent undesired discharge of current near active surface 72. Because the temperatures near active surface 72 can reach thousands of degrees Celsius, insulating piece 54 is made of a material that can withstand these extreme temperatures.

While insulating piece 54 has been illustrated as a circular piece with an aperture for placing the electrode 50, insulating piece 54 can be made to have any desired shape. Typically the shape of insulating piece 54 is advantageously designed so as to correspond to the shape of the electrode 50. Insulating piece 54 is usually configured to provide spacing between the active surface 72 and other materials that make up part of probe 40, such as a heat resistant coating.

Figure 4:
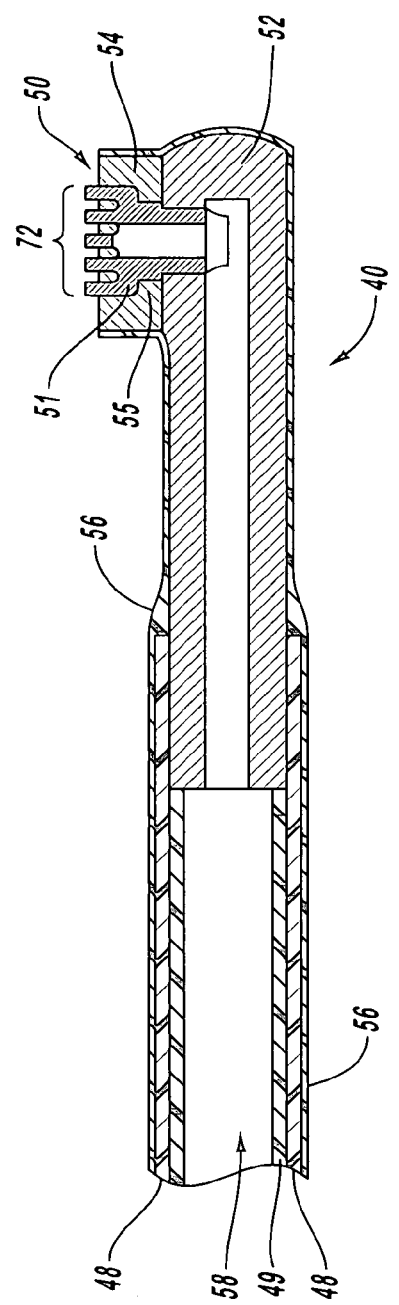
FIG. 4 is a cross-sectional view of the probe of the electrosurgical instrument of FIG. 2.

As further shown in FIGS. 3 and 4, electrode seat 52 provides a location for connecting electrode 50 at a desired angle. In an exemplary embodiment, electrode seat 52 includes a bore 53 for connecting electrode 50 at about a 90° angle. Of course electrode seat 53 can be configured to connect electrode 50 at desired angles other than 90°.

Electrode seat 52 can be made from an electrically conductive material such as stainless steel or titanium. In one embodiment, electrode seat 52 forms part of the electrical connection between generator 12 (FIG. 1) and electrode 50.

In one embodiment the connection between electrode 50 and electrode seat 52 secures insulating piece 54 to probe 40. To secure insulating piece 54, electrode 54 includes a retaining ledge 51 that is configured to engage a lip 55 on insulating piece 54. As electrode 50 is connected to electrode seat 52, electrode 50 engages insulating piece 54 and secures it to probe 40. In an exemplary embodiment, electrode 50 is connected to electrode seat 52 through a projection weld.

An end of electrode seat 52, opposite to electrode 50 is inserted into tubing 48. In an exemplary embodiment, tubing 48 and electrode seat 52 are made of an electrically conductive material such that when electrode seat 52 is inserted into tubing 48, they form and electrical connection. For example, electrode seat 50 and tubing 48 can comprise stainless steal or titanium. Electrode seat 52 can be permanently connected to tubing 48 by making a weld at the seam between the end of tube 48 and electrode seat 52. For example, electrode seat 52 can be welded to tubing 48 using a laser. An optional liner 49 within tubing 48 is shown, which can be made of any desired material, including insulating and non-insulating materials.

As shown in FIG. 4, probe 40 also includes an insulating coating 56. Insulating coating 56 is typically formed as one or more electrically insulating sheaths or coatings. Insulating coating 56 prevents direct electrical contact between the metal components of probe 40 and any exterior materials. Any contact between the conductive components of probe 40 and exterior materials can result in unwanted discharge.

Because of the high temperatures involved in electrosurgery, insulating coating 56 can be made from a heat resistant material. Suitable materials for making insulating coating 56 include polytetraflouroethylene, polyimides, and the like. Insulating coating 56 can also include nylon.

In one embodiment electrode 50, seat 52 and tubing 48 define a lumen 58 through the center of probe 40. Lumen 58 opens near the distal end of electrode 50 for aspirating fluids, gasses, and debris from the exterior of probe 40. On the proximal end of probe 40, lumen 58 is connected to aspirator 14 (See FIG. 1), which creates negative pressure in lumen 58. The negative pressure draws gasses, fluids, and debris from the exterior of instrument 10 into lumen 58. During an electrosurgical procedure, a surgical site is typically irrigated with a saline solution. Thus, as material is drawn out of the surgical site through lumen 58 the material is quickly replaced. Alternatively, saline or another fluid can be inserted into the surgical site to create positive pressure, which causes fluid to flow through lumen 58.

Figure 5B:
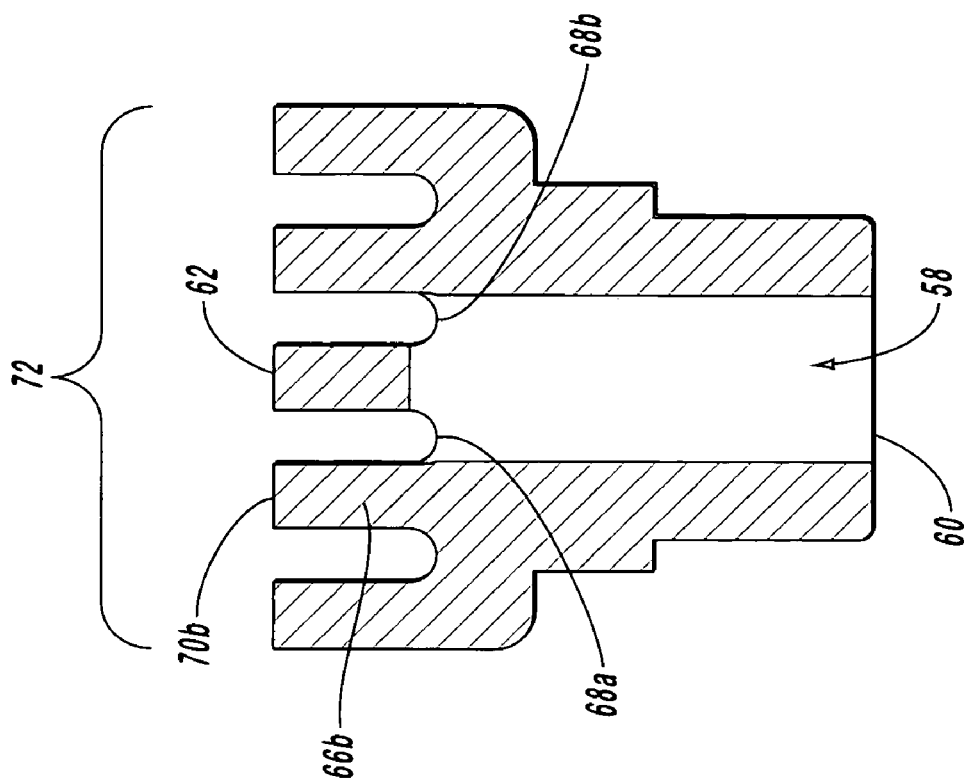
FIG. 5B is a cross-sectional view of the electrode shown in FIG. 3.
Figure 5A:
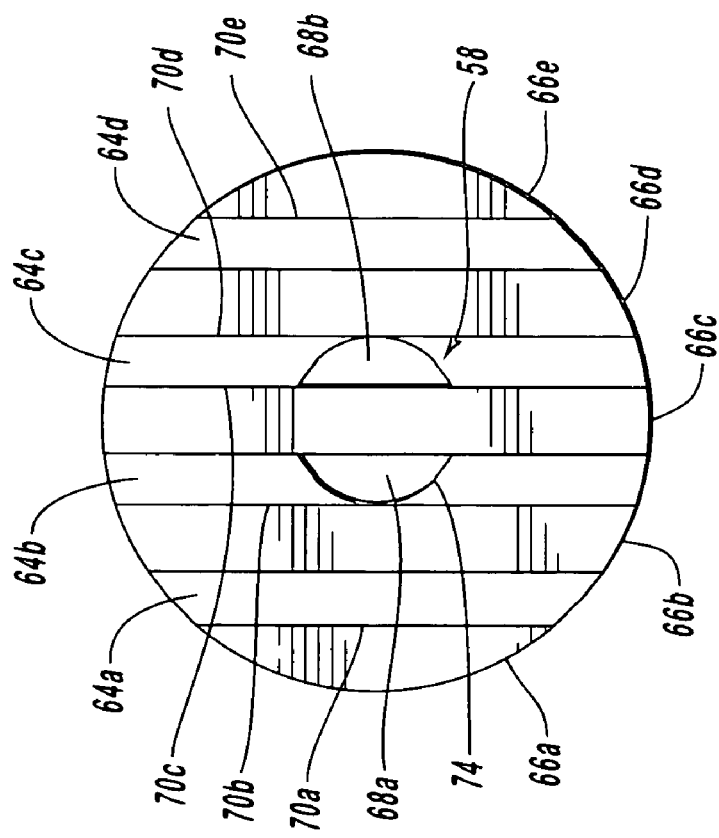
FIG. 5A is a top view of the electrode of the probe shown in FIG. 3.

FIGS. 5A and 5B, show an exemplary electrode 50 according to the present invention. As shown in FIG. 5B, lumen 58 opens at proximal end 60 and terminates prior to distal end 62. Active surface 72 is positioned at distal end 62.

FIG. 5A shows a top view of distal end 62. Grooves 64a–64d (collectively referred to as grooves 64) are formed in distal end 62. Grooves 64b and 64c are formed over lumen 58 to create openings 68a and 68b. As discussed more fully below, rib 66c divides lumen 58 into openings 68a and 68b. Gasses and debris are aspirated into lumen 58 through openings 68a and 68b, via grooves 64b and 64c.

Grooves 64 also define ribs 66a–66e (collectively referred to as ribs 66). Each of ribs 66 has or forms an upper active edge 70a–70e (collectively referred to as upper edges 70).

Active upper edges 70 of electrode 50 are designed to discharge current (i.e. arc) to ablate tissue in an electrosurgical procedure. As discussed above, discharge of current typically occurs where current density is greatest on the electrode. Current density is greatest on small surface areas such as the upper edges 70 of ribs 66. By way of illustration, FIG. 5B shows rib 66a as having an upper active edge 70b. As shown in the top view of FIG. 5A, active edge 70b extends the length of rib 66b. Increasing the number and/or length of the upper edges increases the ablating potential of electrode 50.

In an exemplary embodiment, electrode 50 further includes a lower active edge 74 (FIG. 5A). Lower active edge 74 is formed at the distal end of lumen 58. Lower active edge 74 ablates tissue being aspirated into lumen 58 and prevents tissue from collecting and plugging lumen 58. Lower active edge 74 can be formed at the edge created by a groove, or lower edge 74 can be a wire or other structure configured to ablate tissue that is placed near or at the terminus of electrode. The foregoing and the like are examples of second ablation means for ablating tissue at the distal end of the lumen.

To prevent lumen 58 from plugging, ribs 66 are spaced apart to form a filter above lumen 58. In an exemplary embodiment, ribs 66 are elongate and evenly spaced to form a grate. As shown in FIGS. 5A and 5B, the active edges can form a planar surface for capturing relatively large tissue fragments. Large tissue fragments that can plug lumen 58 are held on the upper active edges until they are ablated to form smaller pieces that are less likely to plug lumen 58.

Fragments that pass through the upper electrodes are typically small enough to pass through opening 68a or 68b.

If not, lower active edge 74 is able to ablate any fragment too large to pass through opening 68a or 68b. Lower active edge 74 can also ablate small particles that could otherwise collect to plug lumen 58. In addition, dividing the opening of lumen 58 into openings 68a and 68b allows gasses and debris to be aspirated through one opening if the other opening is plugged.

Because the upper active edges are spaced to form a grate or filter, gas bubbles and fluids can enter lumen 58 even while large fragments are captured on the upper edges and ablated. In an exemplary embodiment, grooves 64 span distal end 62 such that openings 68a and 68b are elongate, thereby providing a long opening where gasses can be aspirated. The long narrow nature of grooves 64 allows electrode 50 to capture large fragments yet avoid becoming plugged. Fragments are rarely if ever large enough to span the entire groove 64.

In one embodiment, grooves 64 extend to the perimeter of electrode 50 and below the surface of distal end 62. In this embodiment, grooves 64 create openings that extend down the side of electrode 50. Distal end 62 extends beyond insulating piece 54 (See FIG. 4) such that grooves 64 provide a lateral opening to the exterior of probe 40. In this situation, a fragment can cover the entire surface of distal end 62 and gasses can still be aspirated into lumen 58 through the side openings of grooves 64. The ability of the electrosurgical device of the present invention to simultaneously ablate captured tissue fragments and aspirate gasses and fluids allows a surgeon to carry out an electrosurgical procedure with fewer interruptions.

In an exemplary embodiment, the dimensions of electrode 50 are sufficiently small so probe 40 can fit in a portal for performing an arthroscopic procedure. In one embodiment, electrode 50 has a diameter of about 0.10 inch and a length of about 0.11 inch. In an exemplary embodiment, electrode includes grooves of about 0.01 inch wide and ribs about 0.012 inch wide. In a preferred embodiment, the spacing of the active edges is less than about 0.03 inch and more preferably less than about 0.015 inch. Of course, electrodes having different dimensions are within the scope of the present invention.

While exemplary embodiments have been described showing a single electrode with linear and evenly spaced ribs, those skilled in the art will recognize that the electrode of the present invention can be configured differently. In one embodiment, the electrode includes ribs that are taller or shorter or non-linear. In addition, ribs 66 can be of variable height such that active edges 70 do not form a planar surface. In another embodiment, upper active edges 70 and lower active edge 74 are electrically isolated such that electrical parameters can be controlled separately.

Furthermore, active edges 70 are not limited to a corner edge or flat surfaces. For example, in one embodiment, an active edge can include a rounded surface, wire loops, protruding wires, or any other shape with a surface area small enough to provide sufficient current density for creating an arc or high voltage discharge. The foregoing and the like are examples of first ablation means for ablating tissue and filtering tissue being aspirated into a lumen Embodiments of the present invention also include methods for manufacturing electrode 50. In an exemplary embodiment, electrode 50 is manufacture by first shaping or forming a piece of electrically conducting material. The electrically conducting material can include tungsten, stainless steel or its alloys, platinum or its alloys, titanium or its alloys, molybdenum or its alloys, nickel or its alloys, and the like.

In an exemplary embodiment, lumen 58 is created by back drilling proximal end 60 of electrode 50. Lumen 58 opens at proximal end 60 and terminates short of distal end 62. Lumen 58 can be cut to any desired shape such as rectangular or cylindrical. Typically lumen 58 is cut using a drill bit that forms a cylindrical lumen.

Grooves 64 are cut into distal end 62 to form ribs 66. The depth of grooves 64 controls the height of ribs 66. In one embodiment, grooves 64b and 64c are formed to leave rib 66c centered over lumen 58. Grooves 64b and 64c are also cut beyond the terminal end of lumen 58 to create openings 68a and 68b. Rib 66c acts as a barrier between opening 68a and 68b such that tissue blocking opening 68a cannot block opening 68b and vice versa.

Extending grooves 64b and 64c beyond the terminal end of lumen 58 also creates lower active area 74. Grooves 64 are cut so as to cross over lumen 58. Active surface 74 is formed where the terminus of the lumen 58 is exposed by grooves 64b and 64c. In an alternative embodiment, lumen 58 can be larger or smaller and grooves 64 can be cut to create more or fewer openings in lumen 58.

Manufacturing electrode 50 according the present invention is advantageous because it is simple and inexpensive. Because electrodes used in electrosurgical procedures must be very small to insert them through a portal, the manufacturing can be difficult and expensive. The methods of the present invention provide a simple and economical process for manufacturing electrodes.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical instrument for ablating tissue in a surgical procedure comprising:
   an elongate electrically conductive probe having a proximal end portion and a distal end portion and defining a lumen therethrough for aspirating gasses and debris;
   an electrically conductive seat disposed within the probe; and
   an electrode disposed at the distal end portion of the probe and electrically coupled to the electrically conductive seat, the electrode having a distal end and a proximal end, the electrode comprising:
      a lumen, in fluid communication with the lumen of the probe, extending from the proximal end of the electrode toward the distal end and being configured for aspirating gasses and debris therethrough;
      a plurality of upper active edges formed at the distal end of the electrode for ablating tissue, the upper active edges being spaced apart so as to form one or more openings in fluid communication with the lumen of the electrode; and
      at least one lower active edge formed between the upper active edges and the lumen of the electrode for ablating tissue that may otherwise block said lumen.

2. An electrosurgical instrument according to claim 1, wherein said plurality of upper active edges form a planar surface.

3. An electrosurgical instrument according to claim 1, wherein said upper active edges form a grate.

4. An electrosurgical instrument according to claim 1, wherein the electrode is a single piece.

5. An electrosurgical instrument according to claim 1, wherein the spacing between said upper active edges is less than about 0.02 inch.

6. An electrosurgical instrument according to claim 1, wherein the spacing between said upper active edges is less than about 0.01 inch.

7. An electrosurgical instrument according to claim 1, wherein said lower active edge is formed by the terminal end of said lumen of the electrode.

8. An electrosurgical instrument according to claim 1, wherein an upper active edge is positioned over said lumen of the electrode to create a plurality of distinct openings thereto.

9. An electrosurgical instrument according to claim 1, wherein the electrode comprises a material selected from the group consisting of tungsten, stainless steel, platinum, titanium, molybdenum, nickel, alloys thereof, and combinations thereof.

10. An electrosurgical instrument according to claim 1, further comprising an insulator encircling said electrode so as to leave only the distal end of said electrode exposed to the exterior of the electrosurgical instrument.

11. An electrosurgical instrument for ablating tissue in a surgical procedure comprising:
an elongate electrically conductive probe having a proximal end portion and a distal end portion and defining a lumen therethrough for aspirating gasses and debris;
an electrically conductive seat disposed within the probe; and
an electrode disposed at the distal end portion of the probe and electrically coupled to the electrically conductive seat, the electrode having a distal end and a proximal end, the electrode comprising:
a lumen, in fluid communication with the lumen of the probe, extending from the proximal end of the electrode toward the distal end and being configured for aspirating gasses and debris therethrough;
a plurality of upper active edges formed at the distal end of the electrode for ablating tissue, the upper active edges being elongate and spaced apart so as to form a plurality of elongate openings in fluid communication with the lumen of the electrode; and
at least one lower active edge formed at a distal end of the lumen of the electrode for ablating tissue that may otherwise block said lumen.

12. An electrosurgical instrument according to claim 11, wherein said plurality of upper active edges form a planar surface.

13. An electrosurgical instrument according to claim 11, wherein said upper active edges form a grate.

14. An electrosurgical instrument according to claim 11, wherein an upper active edge is positioned over said lumen to create a plurality of distinct openings thereto.

15. An electrosurgical instrument for ablating tissue in a surgical procedure comprising:
an elongate electrically conductive probe having a proximal end portion and a distal end portion and defining a lumen therethrough for aspirating gasses and debris; and
an electrode disposed at the distal end portion of the probe, the electrode having a distal end and a proximal end, the electrode comprising:
a lumen, in fluid communication with the lumen of the probe, extending from the proximal end of the electrode toward the distal end and being configured for aspirating gasses and debris therethrough; and
a plurality of upper active edges formed at the distal end of the electrode for ablating tissue, the upper active edges being elongate and spaced apart to form at least one elongate groove that spans the distal end of the electrode, the groove being positioned over the lumen of the electrode and in fluid communication therewith, the groove providing an opening at the distal end of the electrode and also lateral openings on opposite sides of the electrode for aspirating gasses and debris therethrough.

16. An electrosurgical instrument according to claim 15, wherein the upper active edges form a plurality of grooves that are in fluid communication with the lumen of the electrode.

17. An electrosurgical instrument according to claim 15, wherein the groove is narrower than the diameter of the lumen of the electrode.

18. An electrosurgical instrument according to claim 15, wherein the groove is narrower than half the diameter of the lumen of the electrode.

19. An electrosurgical instrument according to claim 15, wherein the upper active edges form a surface having a perimeter and wherein the groove creates an opening at the perimeter of the electrode that extends below the surface, the opening being in fluid communication with the exterior of the electrosurgical instrument.

20. An electrosurgical instrument for ablating tissue in a surgical procedure comprising:
an elongate electrically conductive probe having a proximal end portion and a distal end portion and defining a lumen therethrough for aspirating gasses and debris;
an electrically conductive seat disposed within the probe; and
an electrode disposed at the distal end portion of the probe and electrically coupled to the electrically conductive seat, the electrode having a distal end and a proximal end, the electrode comprising:
aspiration means for aspirating gasses and debris through the electrode and into the lumen of the probe;
first ablation means, disposed at the distal end of the electrode, for ablating tissue; and
second ablation means, disposed between the distal end and proximal end, for ablating tissue that may otherwise block said aspiration means; and
an insulating piece disposed around a portion of the electrode and having a proximal end and a distal end, wherein the proximal end of the electrode extends beyond the proximal end of the insulating piece and wherein the distal end of the electrode extends beyond the distal end of the insulating piece.

21. An electrosurgical instrument according to claim 20, wherein said first ablation means comprises a plurality of upper active edges spaced apart so as to form one or more openings in fluid communication with the lumen.

22. An electrosurgical instrument according to claim 20, wherein said second ablation means comprises a lower active edge formed between the upper active edges and the lumen for ablating tissue that may otherwise block said lumen.

* * * * *

UNITED STATES PATENT AND TRADEMARK OFFICE
CERTIFICATE OF CORRECTION

PATENT NO. : 7,150,746 B2 Page 1 of 1
APPLICATION NO. : 10/866014
DATED : December 19, 2006
INVENTOR(S) : DeCesare et al.

It is certified that error appears in the above-identified patent and that said Letters Patent is hereby corrected as shown below:

Column 3
Line 47, change "blow" to --below--

Signed and Sealed this

Eighteenth Day of September, 2007

JON W. DUDAS
*Director of the United States Patent and Trademark Office*